United States Patent
Matsuo et al.

(10) Patent No.: US 10,863,896 B2
(45) Date of Patent: Dec. 15, 2020

(54) ENDOSCOPE SYSTEM AND FLUORESCENCE IMAGING METHOD

(71) Applicant: PANASONIC I-PRO SENSING SOLUTIONS CO., LTD., Fukuoka (JP)

(72) Inventors: Naoto Matsuo, Fukuoka (JP); Haruhiko Kohno, Fukuoka (JP); Nobuhiro Tsuchihashi, Fukuoka (JP)

(73) Assignee: PANASONIC I-PRO SENSING SOLUTIONS CO., LTD., Fukuoka (JP)

( * ) Notice: Subject to any disclaimer, the term of this patent is extended or adjusted under 35 U.S.C. 154(b) by 228 days.

(21) Appl. No.: 15/702,074

(22) Filed: Sep. 12, 2017

(65) Prior Publication Data

US 2018/0070806 A1 Mar. 15, 2018

(30) Foreign Application Priority Data

Sep. 13, 2016 (JP) ................................. 2016-178798

(51) Int. Cl.
*A61B 1/07* (2006.01)
*A61B 1/06* (2006.01)
(Continued)

(52) U.S. Cl.
CPC ........ *A61B 1/0646* (2013.01); *A61B 1/00009* (2013.01); *A61B 1/00045* (2013.01);
(Continued)

(58) Field of Classification Search
None
See application file for complete search history.

(56) References Cited

U.S. PATENT DOCUMENTS

| 2012/0010465 A1 | 1/2012 | Erikawa et al. | |
| 2017/0209050 A1* | 7/2017 | Fengler | H04N 9/045 |
| 2018/0303573 A1* | 10/2018 | Trulson | G02B 21/06 |

FOREIGN PATENT DOCUMENTS

| EP | 2404544 A1 * | 1/2012 | ........... A61B 1/0669 |
| JP | 2007-143624 A | 6/2007 | |

(Continued)

OTHER PUBLICATIONS

U.S. Appl. No. 15/786,980 to Kenta Watanabe, filed Oct. 18, 2017.
(Continued)

*Primary Examiner* — William C Vaughn, Jr.
*Assistant Examiner* — Joseph Daniel A Towe
(74) *Attorney, Agent, or Firm* — Greenblum & Bernstein, P.L.C.

(57) ABSTRACT

An endoscope system includes a non-visible light source configured to emit first excitation light and second excitation light onto a target, an image sensor configured to generate an image including the target excited by at least one of the first excitation light and the second excitation light to emit fluorescence, and an output device configured to output the image. The first excitation light has a half width of not more than 10 nm and a first wavelength of a non-visible light band. The second excitation light has a half width of not more than 10 nm and a second wavelength of the non-visible light band being different from the first wavelength.

8 Claims, 14 Drawing Sheets

(51) Int. Cl.
*A61B 5/00* (2006.01)
*A61B 1/00* (2006.01)
*A61B 1/04* (2006.01)
*H04N 5/225* (2006.01)

(52) U.S. Cl.
CPC .......... *A61B 1/00186* (2013.01); *A61B 1/043* (2013.01); *A61B 1/0638* (2013.01); *A61B 1/0653* (2013.01); *A61B 1/07* (2013.01); *A61B 5/0071* (2013.01); *A61B 5/0086* (2013.01); *A61B 5/7225* (2013.01); *H04N 5/2256* (2013.01); *H04N 2005/2255* (2013.01)

(56) References Cited

FOREIGN PATENT DOCUMENTS

| | | | | |
|---|---|---|---|---|
| JP | 2012-016545 A | | 1/2012 | |
| JP | 2012016545 A | * | 1/2012 | ........... A61B 1/0653 |
| JP | 5905980 B1 | * | 4/2016 | |
| JP | 5905980 B1 | | 4/2016 | |

OTHER PUBLICATIONS

Office Action issued in Japan family member Patent Appl. No. 2016-178798, dated Mar. 27, 2018, along with an English-language translation thereof.

* cited by examiner

ENDOSCOPE SYSTEM AND FLUORESCENCE IMAGING METHOD

CROSS REFERENCE TO RELATED APPLICATIONS

This application is based on Japanese Patent Application (No. 2016-178798) filed on Sep. 13, 2016, the contents of which are incorporated herein by reference.

BACKGROUND OF THE INVENTION

1. Field of the Invention

The present disclosure relates to an endoscope system and a fluorescence imaging method.

2. Description of the Related Art

In the background art, there has been known a fluorescence imaging device which uses an LED (Light Emitting Diode) (see JP-A-2007-143624). The fluorescence imaging device irradiates a target with excitation light having a wavelength of 750 nm etc. from the LED to cause fluorescence emission at a wavelength of 845 nm etc. in the target, and takes a fluorescence image.

In the fluorescence imaging device described in JP-A-2007-143624, light intensity of the fluorescence emission may decrease in some target, causing deterioration in accuracy of the fluorescence imaging.

SUMMARY OF THE INVENTION

The present disclosure has been accomplished in consideration of the aforementioned circumstances. An object of the present disclosure is to provide an endoscope system and a fluorescence imaging method in which reduction of light intensity of fluorescence emission generated by a target can be inhibited so that accuracy of fluorescence imaging can be improved.

The endoscope system according to the present disclosure includes: a non-visible light source configured to emit first excitation light and second excitation light onto a target, the first excitation light having a half width of not more than 10 nm and a first wavelength of a non-visible light band, the second excitation light having a half width of not more than 10 nm and a second wavelength of the non-visible light band different from the first wavelength; an image sensor configured to generate an image including the target excited by at least one of the first excitation light and the second excitation light to emit fluorescence; and an output device configured to output the image.

The fluorescence imaging method according to the present disclosure is a fluorescence imaging method in an endoscope system, including: emitting first excitation light and second excitation light onto a target, the first excitation light having a half width of not more than 10 nm and a first wavelength of a non-visible light band, the second excitation light having a half width of not more than 10 nm and a second wavelength of the non-visible light band different from the first wavelength; generating an image including the target that is excited by at least one of the first excitation light and the second excitation light to emit fluorescence; and outputting the image.

According to the present disclosure, reduction of light intensity of fluorescence emission generated by a target can be inhibited so that accuracy of fluorescence imaging can be improved.

DETAILED DESCRIPTION OF THE EXEMPLARY EMBODIMENTS

An embodiment will be described below in detail with reference to the drawings if necessary. Detailed description more than necessary may be omitted. For example, detailed description about any matter which has been already known well or duplicated description about substantially the same configuration may be omitted. This is to avoid unnecessary redundancy in the following description in order to facilitate understanding of those skilled in the art. Incidentally, the accompanying drawings and the following description are provided so that those skilled in the art can understand the present disclosure fully. The accompanying drawings and the following description are not intended to limit the subject matter described in Claims.

(Details Up to when Mode of Present Disclosure is Obtained)

In an operation using an endoscope, the following procedure may be taken. That is, ICG (IndoCyamine Green) which is a fluorescent substance is given in vivo, near infrared light is applied to a tumor region (affected part) etc. where the ICG is excessively accumulated, so as to cause light emission in the affected part, and the region including the affected part is imaged. When the ICG is excited by the excitation light, fluorescence as light with a longer wavelength is emitted.

Intensity of the light generated as the fluorescence is weaker than that of the excitation light. When light intensity of the excitation light is regarded as 100, the light intensity of the fluorescence is about 5 to 6. In addition, when a wavelength band of irradiation light generated by an LED is broad and a wavelength band of the excitation light and a wavelength band of the fluorescence are near to each other, the wavelength band of the irradiation light generated by the LED and the wavelength band of the fluorescence may overlap with each other. For this reason, an IR excitation light cut filter is often provided in front of an image sensor in order to prevent fluorescence imaging from being hindered by the excitation light.

Figure 15:
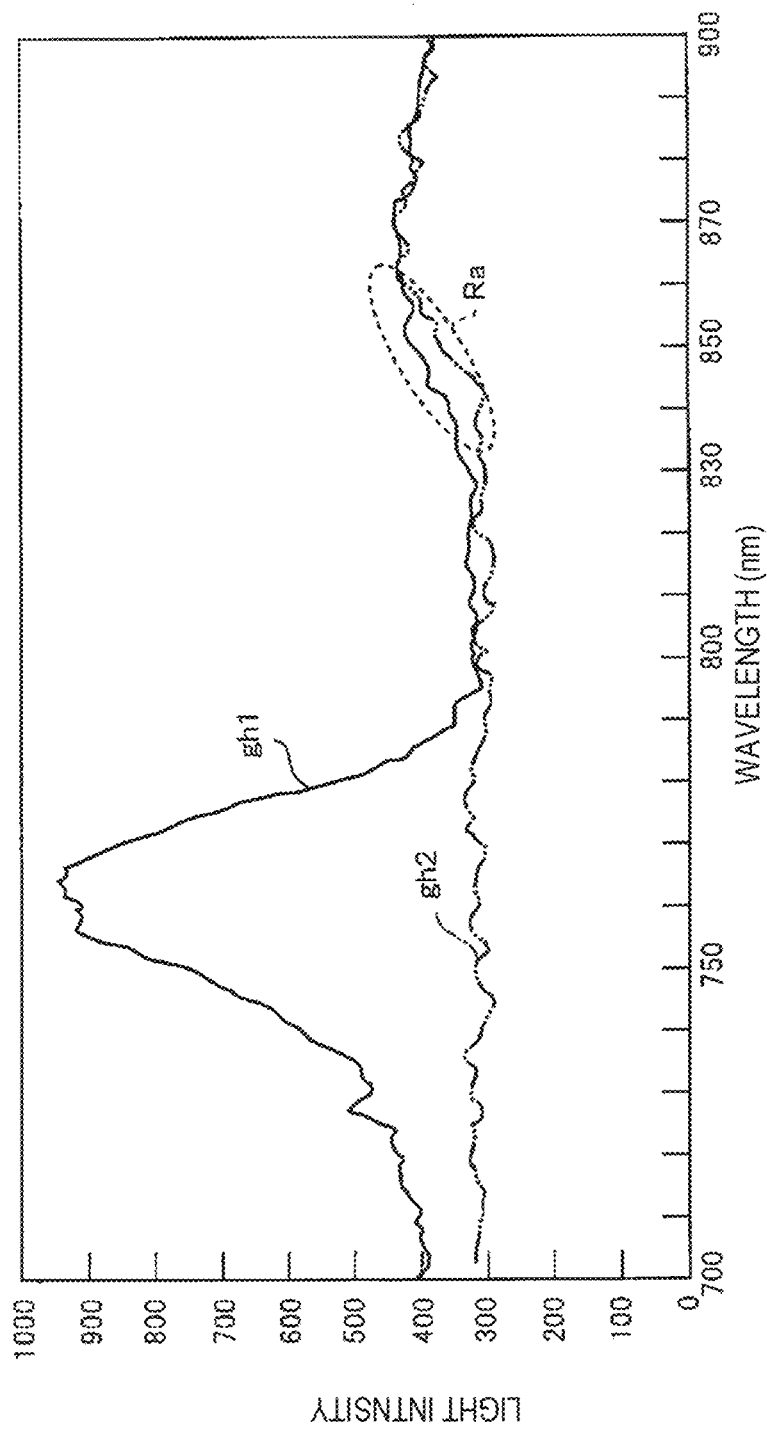
FIG. 15 is a graph showing light intensities of fluorescence emissions from a target, which are obtained between when the IR excitation light cut filter is provided and when no IR excitation light cut filter is provided.

FIG. 15 is a graph showing light intensities of fluorescence emissions from a target, which are obtained when such an IR excitation light cut filter is provided and when no IR excitation light cut filter is provided. In FIG. 15, a graph gh1 shows the light intensity in the case where no IR excitation light cut filter is provided. A graph gh2 shows the light intensity in the case where the IR excitation light cut filter is provided. The IR excitation light cut filter has the following specification. That is, transmittance of the IR excitation light cut filter is not higher than 1%, for example, in a wavelength range of from 665 nm to 840 nm.

When the IR excitation light cut filter is provided, a wavelength band of the fluorescence may be included in a portion of a wavelength band shielded by the IR excitation light cut filter. In FIG. 15, the light quantity of the fluorescence emission is reduced when the IR excitation light cut filter is provided in a band of 835 nm to 865 nm (see a dotted line circle Ra in FIG. 15) whereas the band of the fluorescence emission is 830 nm to 900 nm. When the IR excitation light cut filter is provided thus, the light intensity of the fluorescence may be weaker. In addition, the IR excitation light cut filter shields a signal of the wavelength band where the excitation light is absorbed. Accordingly, the fluorescence emission generated based on the excitation light of the LED may be also weaker.

Therefore, when irradiation light to be generated by not the LED but a laser diode (LD) is used, a wavelength band of the irradiation light generated by the LD is narrower than a wavelength band of irradiation light generated by the LED.

On the other hand, the wavelength band of the irradiation light generated by the LED is not limited to 750 nm but various wavelength bands may be used. The wavelength band of the fluorescence is also not limited to 845 nm but various wavelength bands may be used. This is because a mode of the fluorescence emission in reaction to the excitation light varies according to a concentration of a chemical such as the ICG or a physical condition of a patient which is the target.

Accordingly, when the LD excitation light narrower in band is used, the LD excitation light may be deviated from a wavelength band suitable for the fluorescence emission in some target (object to be inspected). Thus, the fluorescence emission may be insufficient to cause difficulty in fluorescence imaging.

An endoscope system and a fluorescence imaging method in which reduction of light intensity of fluorescence emission generated by a target can be inhibited so that accuracy of fluorescence imaging can be improved will be described below.

First Embodiment

[Configuration, etc.]

Figure 1:
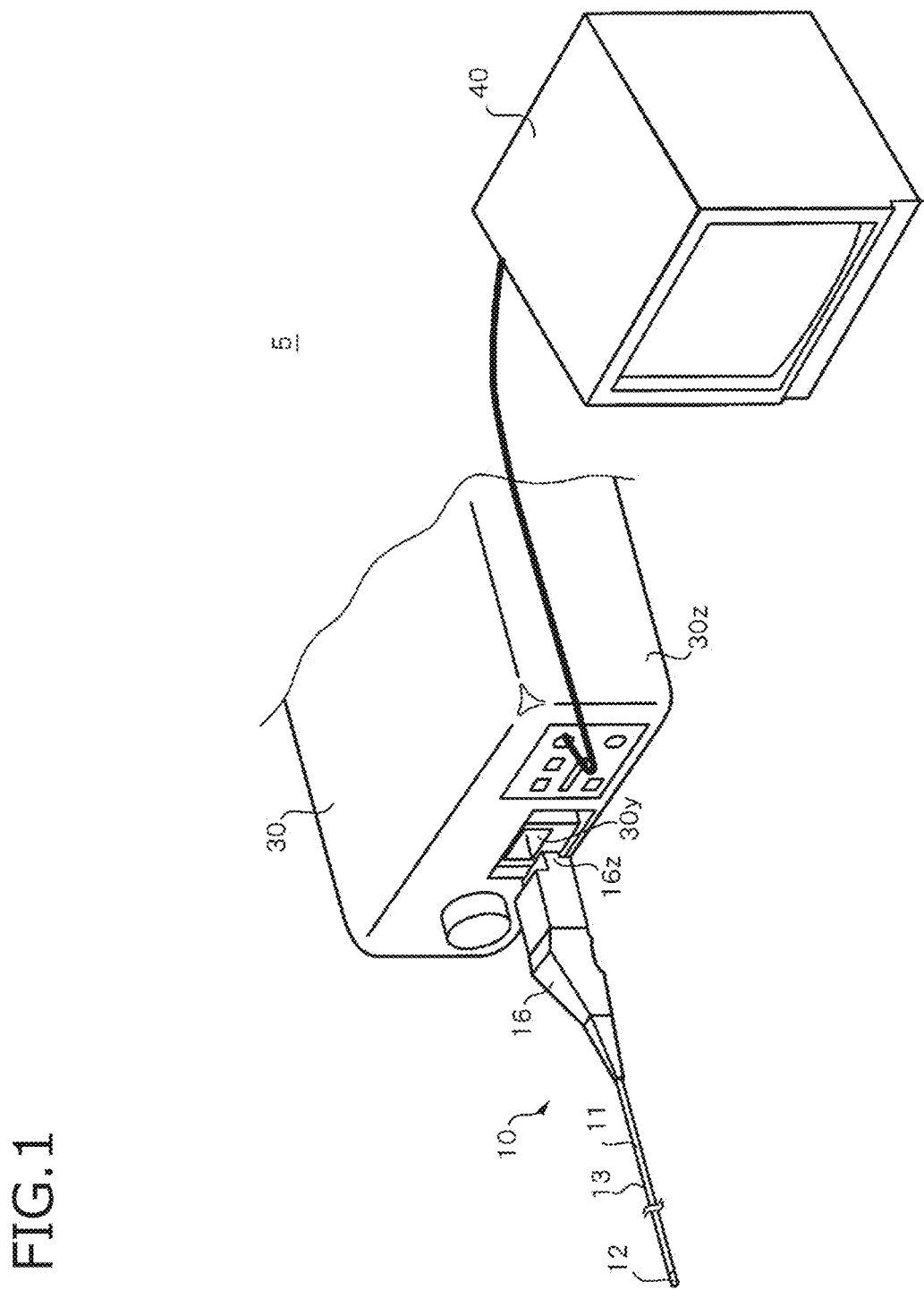
FIG. 1 is a perspective view showing an example of external appearance of an endoscope system in a first embodiment.

FIG. 1 is a perspective view showing an example of external appearance of an endoscope system 5 in a first embodiment. As expressions to be used herein, an up direction and a down direction of a video processor 30 placed on a horizontal surface will be referred to as "up" and "down" respectively. In addition, a side where an endoscope 10 images a subject to be observed will be referred to as "front (distal)", and a side where the endoscope 10 is connected to the video processor 30 will be referred to as "rear".

The endoscope system 5 includes the endoscope 10, the video processor 30 and a monitor 40. The endoscope 10 is, for example, a soft endoscope for medical use. The video processor 30 applies image processing on each taken image (including each still image and each moving image) obtained by imaging a subject to be observed (which is regarded as a human body or the interior of a human body in this case). The monitor 40 displays the image in accordance with a display signal outputted from the video processor 30. For example, the image processing includes color correction, gradation correction and gain correction.

The endoscope 10 images the subject to be observed (target). The endoscope 10 is provided with a scope 13 which is inserted into the interior of the subject to be observed, and a plug portion 16 to which a rear end portion of the scope 13 is connected. In addition, the scope 13 includes a comparatively long flexible soft portion 11 and a rigid hard portion 12 provided at a distal end of the soft portion 11. The structure of the scope 13 will be described later.

The video processor 30 has a housing 30z. The video processor 30 applies image processing to the taken image, and outputs a resulting display signal which has been subjected to the image processing. A socket portion 30y into which a proximal end portion 16z of the plug portion 16 is inserted is disposed in a front surface of the housing 30z. The plug portion 16 is inserted into the socket portion 30y so that the endoscope 10 and the video processor 30 can be connected to each other. With this configuration, electric power and various signals (e.g. a video signal and a control signal) can be transmitted/received between the endoscope 10 and the video processor 30. The electric power and the various signals are guided from the plug portion 16 toward the soft portion 11 through a transmission cable (not shown) which has been inserted through the interior of the scope 13. In addition, an image signal outputted from an image sensor 22 (solid-state image sensing device) (see FIG. 2) which is provided inside the hard portion 12 is transmitted to the video processor 30 from the plug portion 16 through the transmission cable. In addition, the soft portion 11 can be moved (e.g. bent) in accordance with an input operation to an operating portion (not shown) of the endoscope 10.

The video processor 30 applies image processing to the image signal transmitted through the transmission cable to thereby convert resulting image data which has been subjected to the image processing into a display signal, and outputs the converted display signal to the monitor 40.

The monitor 40 has a display device such as an LCD (Liquid Crystal Display) or a CRT (Cathode Ray Tube). The monitor 40 displays the image of the target taken by the endoscope 10.

Figure 2:
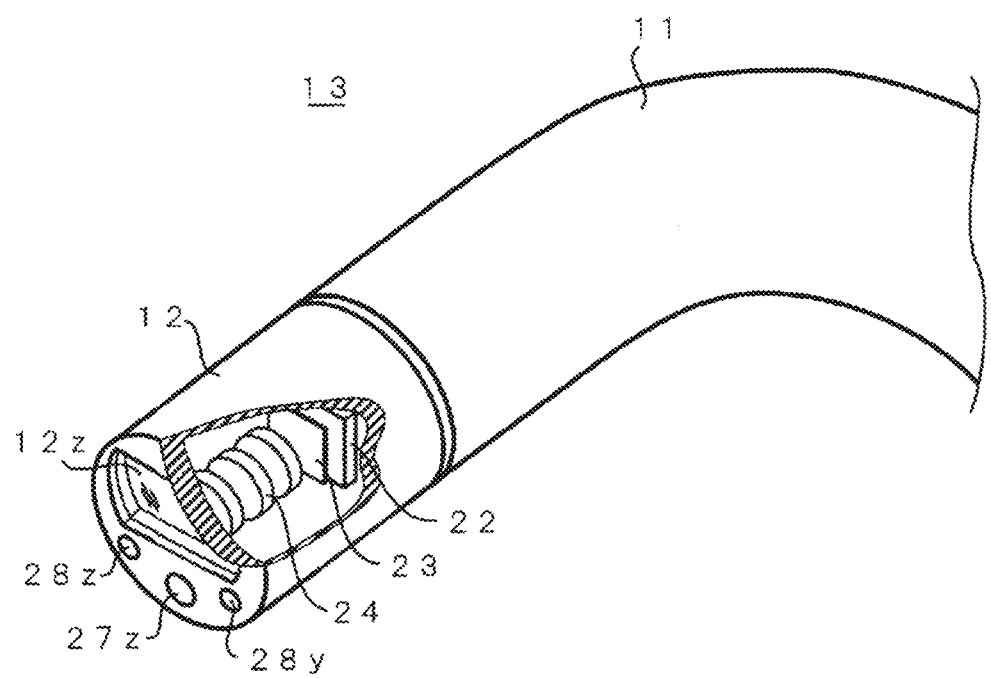
FIG. 2 is a schematic view showing an internal structure of a hard portion provided at a distal end of a scope.

FIG. 2 is a schematic view showing an internal structure of the hard portion 12 provided at the distal end of the scope 13. An image taking window 12z is disposed in a distal end face of the hard portion 12. The image taking window 12z is formed to include an optical material such as optical glass or optical plastic. Light from the target is incident on the image taking window 12z.

An irradiation window 27z in which distal ends of a plurality of (two in this case) optical fibers 27A and 27B are exposed is disposed in the distal end face of the hard portion 12. IR (InfraRed) excitation lights from an IR excitation light source 33 (see FIG. 4) are transmitted through the optical fibers 27A and 27B. As will be described later, laser lights with two wavelengths (e.g. 780 nm and 808 nm) are emitted from the optical fibers 27A and 27B. Irradiation windows 28z and 28y in which a distal end of an optical fiber 28 is exposed are disposed in the distal end face of the hard portion 12. Visible light from a visible light source 34 (see FIG. 4) is transmitted through the irradiation windows 28z and 28y.

Incidentally, the number of the laser lights with different wavelengths emitted from the IR excitation light source 33 or the number of the optical fibers may be three or more. The number of the laser lights or the number of the optical fibers is not limited specially as long as the LDs and the optical fibers can be housed inside the scope 13.

Inside the hard portion 12, a lens 24, an IR excitation light cut filter 23, the image sensor 22 and a first driving circuit 21 (see FIG. 4) are arranged sequentially from the image taking window 12z side. Incidentally, the image sensor 22 and the first driving circuit 21 constitute a sensor unit SU (see FIG. 4). In addition, the number of lenses 24 is not limited to one but may be two or more.

Incident light (light of fluorescence emission, visible light) from the image taking window 12z is condensed by the lens 24 and transmitted through the IR excitation light cut filter 23. Then, the light forms an image on an imaging face of the image sensor 22. In addition, the size (radial length) of the image sensor 22 disposed inside the hard portion 12 of the scope 13 is equal to or smaller than 10 mm. Accordingly, the image sensor 22 can be applied to an endoscope.

In the embodiment, the laser lights having the wavelengths of 780 nm and 808 nm are mainly illustrated. However, laser lights having other wavelengths in the range of 750 nm to 810 nm may be used alternatively. For example, laser lights having wavelengths of 760 nm, 785 nm and 792 nm may be used.

In addition, a difference in wavelength between the excitation lights may be set to be equal to or greater than a predetermined value (20 nm). That is, a difference between a wavelength of first excitation light and a wavelength of second excitation light are distant from each other by 20 nm or more. Thus, the endoscope system 5 can widely cover an excitation light wavelength band (750 nm to 810 nm) suitable for fluorescence emission. In this case, shortage of a light quantity of the fluorescence emission can be prevented from occurring due to the two laser lights inclined to a wavelength band which has little contribution to the fluorescence emission.

Figure 3:
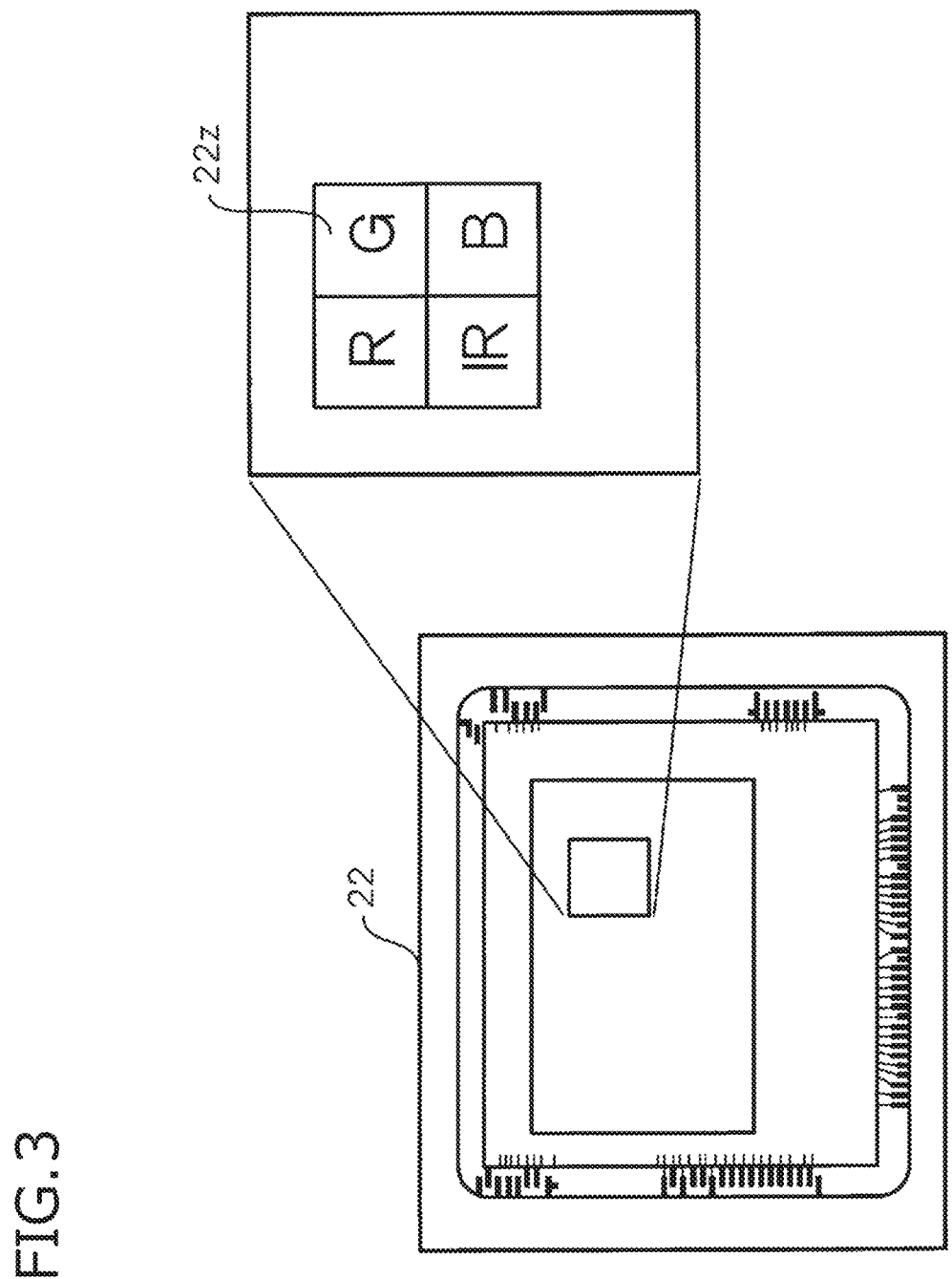
FIG. 3 is a schematic view explaining a structure of an image sensor.

FIG. 3 is a schematic view explaining the structure of the image sensor 22. The image sensor 22 has, for example, color filters 22z arranged into a Bayer array in a front surface of the image sensor 22 so that infrared (IR), red (R), blue (B) and green (G) wavelength lights can be transmitted through the color filters 22z respectively. The image sensor 22 is an image sensing device having a structure in which, for example, IR pixels, red pixels, blue pixels and green pixels for receiving the respective wavelength lights are arrayed.

For example, the image sensor 22 is a solid-state image sensing device such as a CCD (Charge Coupled Device) or a CMOS (Complementary Metal Oxide Semiconductor). The image sensor 22 is used, for example, as a single plate type camera which can receive infrared light, red light, blue light and green light simultaneously.

Figure 4:
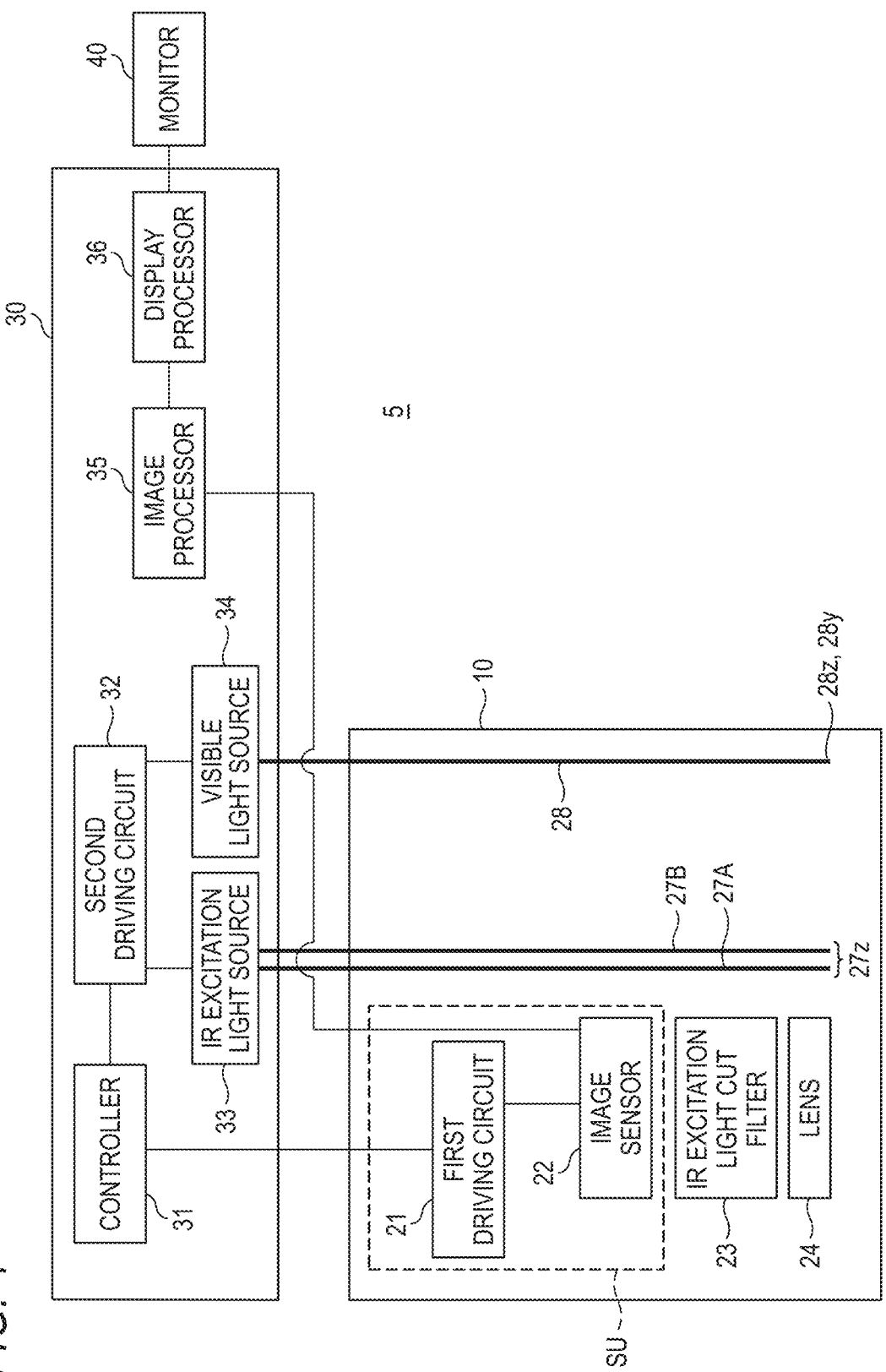
FIG. 4 is a block diagram showing an example of a hardware configuration of the endoscope system.

FIG. 4 is a block diagram showing an example of the hardware configuration of the endoscope system 5. The endoscope 10 is provided with the lens 24, the IR excitation light cut filter 23, the image sensor 22 and the first driving circuit 21 which are provided inside the hard portion 12 of the scope 13, as described above. In addition, the endoscope 10 is provided with the optical fibers 27A, 27B and 28 which are inserted through the interior of the scope 13 to extend from the proximal end portion 16z of the plug portion 16 to the distal end face of the hard portion 12.

The first driving circuit 21 is operated as a driving portion to turn ON/OFF an electronic shutter of the image sensor 22. When the electronic shutter has been turned ON by the first driving circuit 21, the image sensor 22 photoelectrically converts an optical image formed on the imaging face into an image signal and outputs the image signal. In the photoelectric conversion, exposure of the optical image to light and generation or reading of the image signal are performed.

The IR excitation light cut filter 23 is disposed on a front side (light receiving side) of the image sensor 22. Of the light which has been transmitted through the lens 24, the IR excitation light cut filter 23 shields IR excitation lights reflected by the target, but transmits light of fluorescence emission and visible light. The light of fluorescence emission is generated in reaction to the IR excitation lights.

Figure 5:
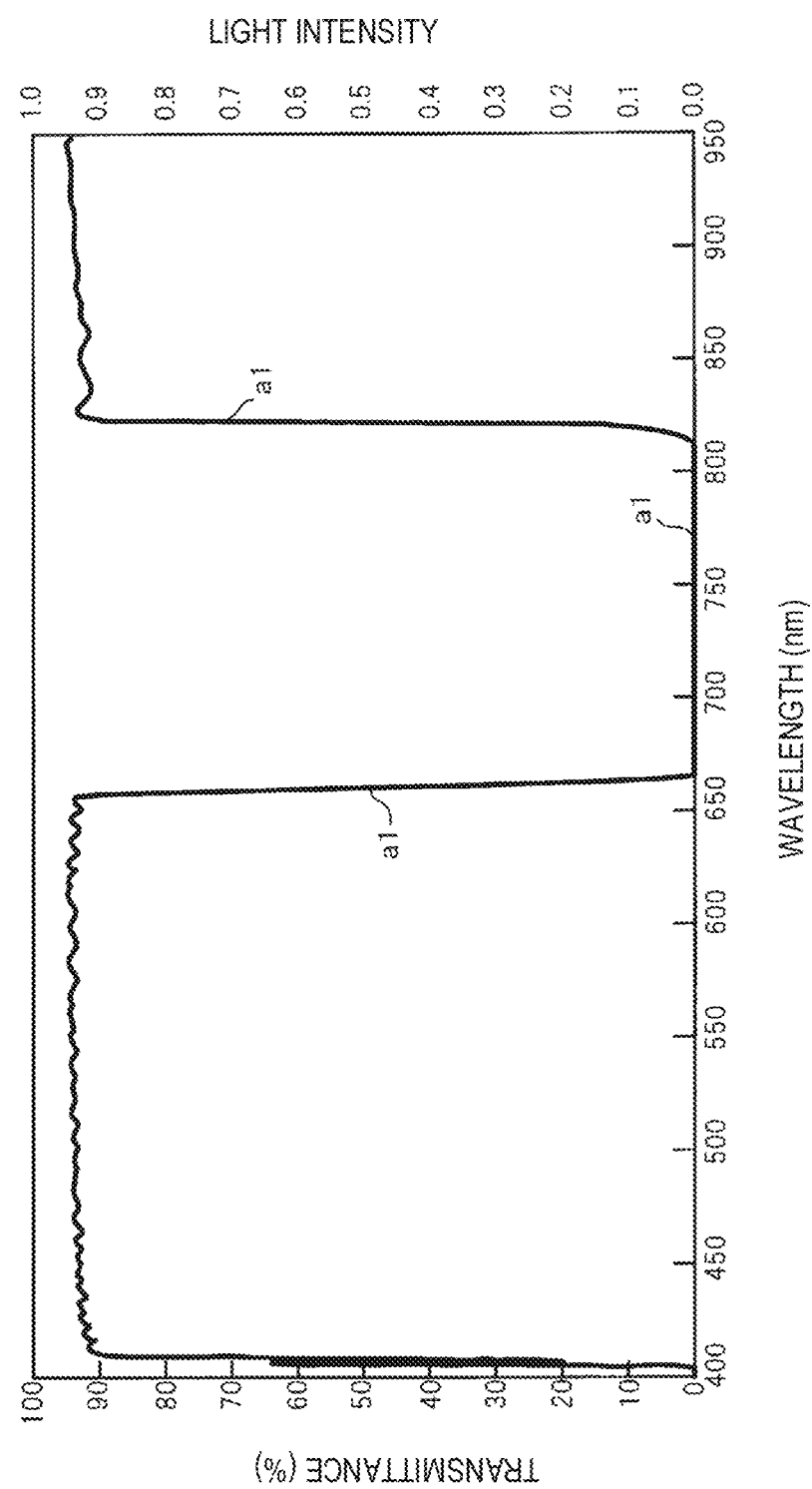
FIG. 5 is a graph showing an example of a characteristic of an IR excitation light cut filter.

FIG. 5 is a graph showing a characteristic of the IR excitation light cut filter 23. In FIG. 5, the reference sign a1 expresses the characteristic of the IR excitation light cut filter 23. ICG which is a fluorescent substance (organic fluorescent pigment) is given into a human body which is a subject to be observed. The ICG is accumulated in an affected part which is a target. When the ICG is excited by IR excitation lights, the ICG generates light of fluorescence emission with a longer wavelength. The wavelengths of the IR excitation lights are, for example, 780 nm and 808 nm. The IR excitation light cut filter 23 has a characteristic that transmittance of the IR excitation light cut filter 23 is 0.1% or less (e.g. 0.01% or less) with respect to light in a wavelength range of 690 nm to 810 nm. Accordingly, the IR excitation light cut filter 23 shields the IR excitation lights with the wavelengths 780 nm and 808 nm.

Accordingly, in the IR excitation light cut filter 23, transmittance of the light of fluorescence emission with a wavelength around 830 nm is high while transmittance of the IR excitation lights with the wavelengths of 780 nm and 808 nm is low, approximately 0%. In addition, for example, transmittance of visible light with a wavelength range of 380 nm to 690 nm is high.

Accordingly, of incident IR light, a light component of a frequency band including the IR excitation lights (whose wavelengths are 780 nm and 808 nm) reflected by the target is shielded by the IR excitation light cut filter 23, but a light component of a frequency band including the light of fluorescence emission (around 830 nm) generated in reaction to the IR excitation light is transmitted by the IR excitation light cut filter 23. Thus, of the IR excitation lights, the IR excitation lights reflected by the target and having no contribution to the fluorescence emission are shielded by the IR excitation light cut filter 23.

As shown in FIG. 4, the video processor 30 is provided with a controller 31, a second driving circuit 32, the IR excitation light source 33, the visible light source 34, an image processor 35, and a display processor 36.

The controller 31 generally controls an image taking operation. The controller 31 performs light emission control on the second driving circuit 32 and performs driving control on the first driving circuit 21 inside the endoscope 10.

For example, the second driving circuit 32 is a light source driving circuit. The second driving circuit 32 drives the IR excitation light source 33 to continuously emit the IR excitation lights. The IR excitation light source 33 is turned ON continuously (continuous lighting) in an image taking period to thereby continuously irradiate the target with the IR excitation lights.

The image taking period shows a period in which an image of a region to be observed is taken by the endoscope 10. The image taking period is, for example, a period between when a user operation for turning ON a switch provided in the video processor 30 or the endoscope 10 is accepted and when a user operation for turning OFF the same switch is accepted.

In addition, the second driving circuit 32 may drive the IR excitation light source 33 to emit the pulsed IR excitation lights at predetermined intervals. In this case, the IR excitation light source 33 is intermittently turned ON (pulse lighting) in the image taking period to irradiate the target with the pulsed IR excitation lights. Incidentally, in the image taking period, a timing of emitting the IR excitation lights but not emitting the visible light is a timing of taking a fluorescence emission image.

Figure 6:
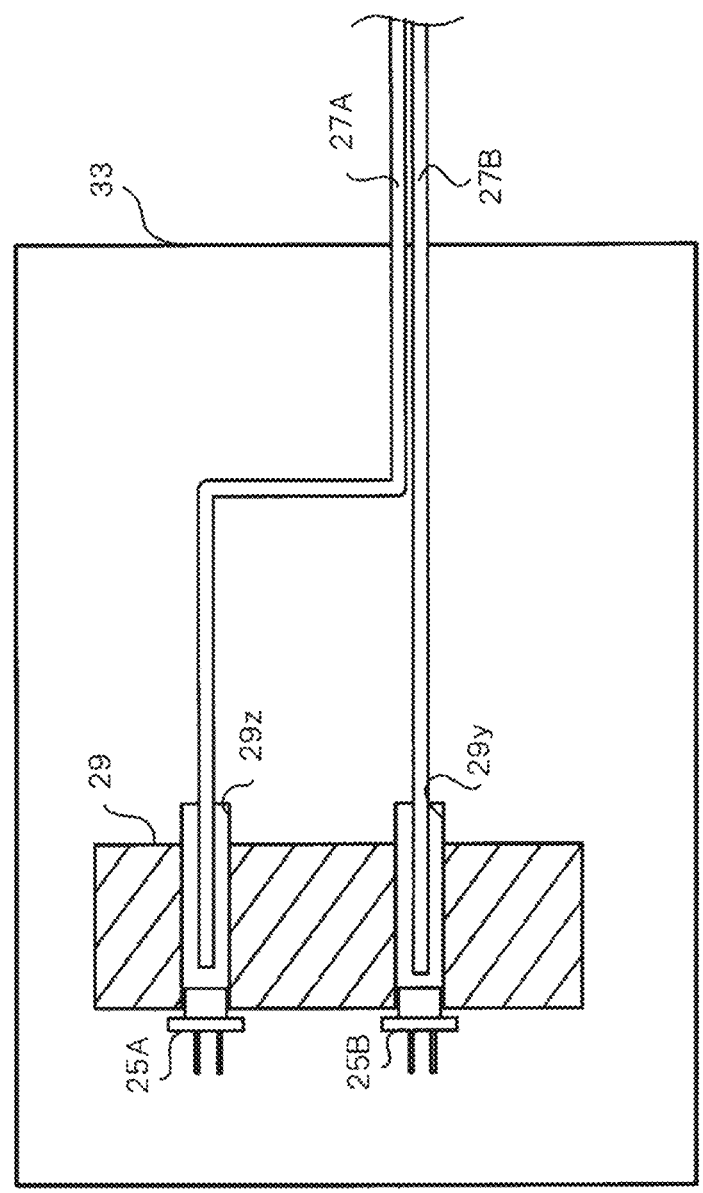
FIG. 6 is a view schematically showing a structure of an IR excitation light source.

The IR excitation light source 33 has LDs 25A and 25B (see FIG. 6). The IR excitation light source 33 outputs laser lights (IR excitation lights) with wavelengths of 780 nm and 808 nm, which are emitted from the LDs 25A and 25B and transmitted through the optical fibers 27A and 27B respectively. Incidentally, as described above, the mode of the fluorescence emission varies according to the concentration of a chemical such as the ICG or a physical condition of a patient which is the target. Accordingly, it is preferable that the laser lights with the wavelengths of 780 nm and 808 nm are emitted simultaneously.

The second driving circuit 32 drives the visible light source 34 to emit pulsed visible light (white light). The visible light source 34 irradiates the target with the pulsed visible light at a timing of taking a visible light image in the image taking period. Incidentally, the light of fluorescence emission is generally weak in brightness. On the other hand, intensive light can be obtained in spite of a short pulse of the visible light.

The image processor 35 applies image processing to the fluorescence emission image and the visible light image outputted alternately from the image sensor 22, and outputs resulting image data which have been subjected to the image processing.

The image processor 35 serves as a gain controller to perform gain adjustment so as to increase a gain of the fluorescence emission image when, for example, luminance of the fluorescence emission image is lower than luminance of the visible light image. The image processor 35 may perform gain adjustment not to increase the gain of the fluorescence emission image but to reduce a gain of the visible light image. The image processor 35 may perform gain adjustment to increase the gain of the fluorescence emission image and reduce the gain of the visible light image. The image processor 35 may perform gain adjustment to increase the gain of the fluorescence emission image more largely than the gain of the visible light image and increase the gain of the visible light image.

The display processor 36 converts the image data outputted from the image processor 35 into a display signal such as an NTSC (National Television System Committee) signal suitable for video display, and outputs the converted display signal to the monitor 40.

The monitor 40 displays the fluorescence emission image and the visible light image, for example, in one and the same region, in accordance with the display signal outputted from the display processor 36. Thus, the user can check the subject to be observed while viewing the fluorescence emission image and the visible light image displayed on the monitor 40.

FIG. 6 is a view schematically showing the structure of the IR excitation light source 33. The IR excitation light source 33 has the LDs 25A and 25B and a heat dissipation housing 29. The heat dissipation housing 29 is formed, for example, to contain aluminum, copper or aluminum nitride. Through holes 29z and 29y are formed in the heat dissipation housing 29.

The optical fibers 27A and 27B are inserted through one sides of the through holes 29z and 29y. The LDs 25A and 25B are engaged with the other sides of the through holes 29z and 29y. Laser lights emitted from the LDs 25A and 25B respectively are incident on incidence faces of the optical fibers 27A and 27B in the through holes 29y and 29z, transmitted through the optical fibers 27A and 27B and guided to the irradiation window 27z as an emission face of the endoscope 10.

In addition, the LDs 25A and 25B thermally touch the heat dissipation housing 29 in the vicinities of opening portions of the through holes 29z and 29y respectively. Heat generated by the LDs 25A and 25B during light emission is transmitted to the heat dissipation housing 29 to be dissipated efficiently. Thus, a change in temperature of each of the LDs 25A and 25B is so small that wavelength shift of the laser lights or fluctuation of the light emission quantities of the laser lights can be suppressed. Accordingly, the endoscope system 5 can obtain IR excitation lights based on the stable laser lights.

[Operation etc.]

Next, an operation example of the endoscope system 5 will be shown.

Figure 7:
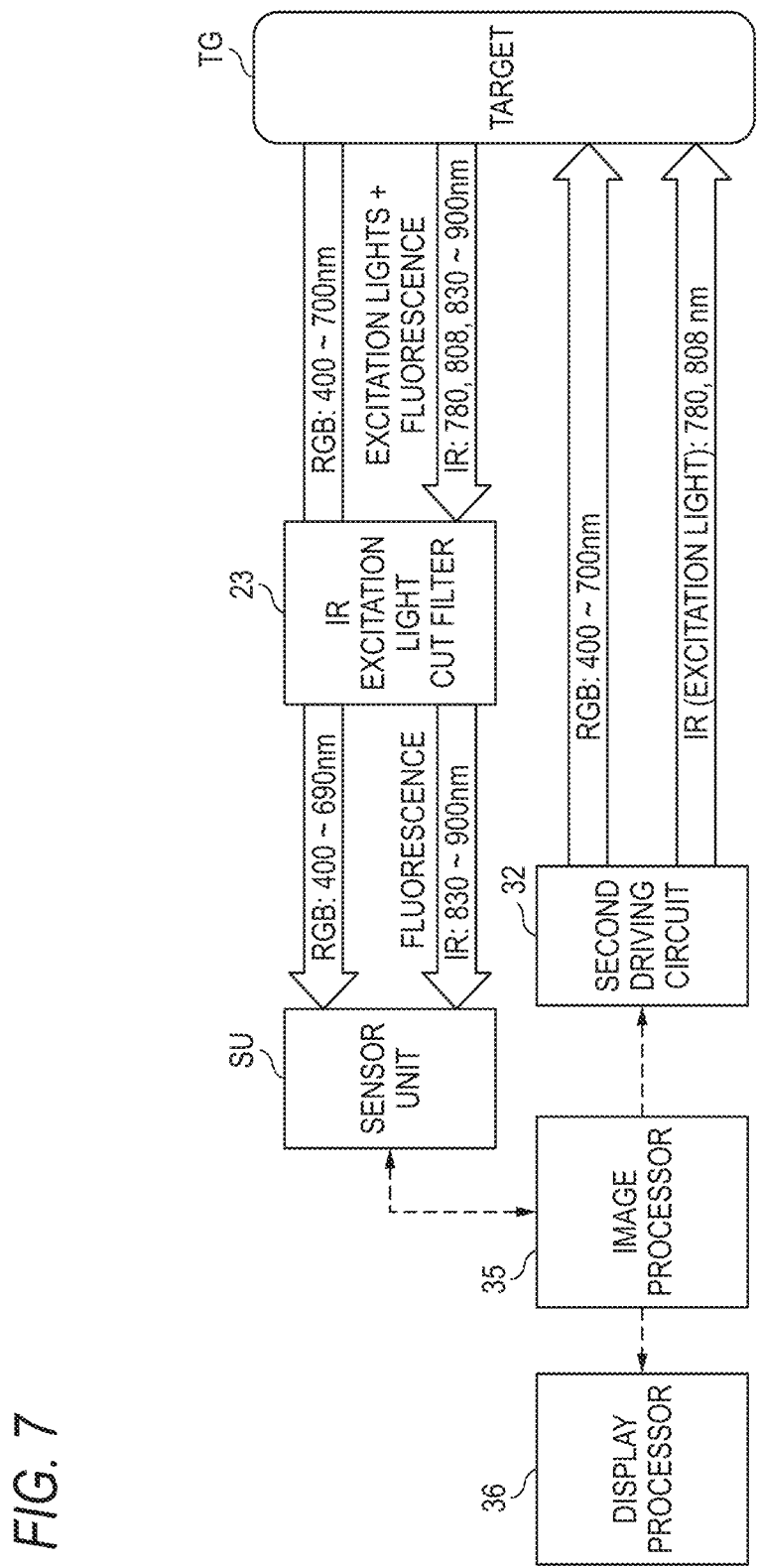
FIG. 7 is a view explaining a flow of irradiating a target with excitation lights to cause fluorescence emission in the target, and receiving the fluorescence from the target.

FIG. 7 is a view explaining a flow of irradiating a target TG with excitation lights to cause fluorescence emission in the target TG, and then receiving the fluorescence from the target TG.

Assume a case in which visible light (RGB light) from the visible light source 34 and excitation lights (IR light) from the IR excitation light source 33 are radiated toward the target TG. The visible light has, for example, a wavelength range of 400 nm to 700 nm, and the excitation lights have, for example, wavelengths of 780 nm and 808 nm. Incidentally, the excitation lights with the wavelengths of 780 nm and 808 nm are merely exemplary. The excitation lights may have other wavelengths as long as the wavelengths are included in the excitation light wavelength band suitable for fluorescence emission. In addition, the number of the excitation lights may be three or more.

The visible light is reflected by the target TG, transmitted through the IR excitation light cut filter 23 and received by the image sensor 22. As described above, the IR excitation light cut filter 23 shields transmission of light with the wavelength range of 690 nm to 810 nm. Accordingly, of the visible light reflected by the target TG, for example, only light having a band of 690 nm to 700 nm is partially cut. Therefore, a large portion of the visible light is still received by the image sensor 22 inside the sensor unit SU.

On the other hand, when the ICG used in the embodiment is excited by the IR excitation lights, the ICG emits fluorescence as light having a wavelength range of 830 nm to 900 nm (e.g. 830 nm). The IR light emitted from the target TG includes the excitation lights (750 nm to 810 nm, e.g. wavelengths of 780 nm and 808 nm) reflected by the target, and the fluorescence (830 nm to 900 nm) emitted from the target. When the IR light is transmitted through the IR excitation light cut filter 23, of the IR light, transmission of the lights having the wavelength range of 750 nm to 810 is shielded but the fluorescence having the wavelength range of 830 nm to 900 nm is received by the image sensor 22 inside the sensor unit SU.

Figure 8:
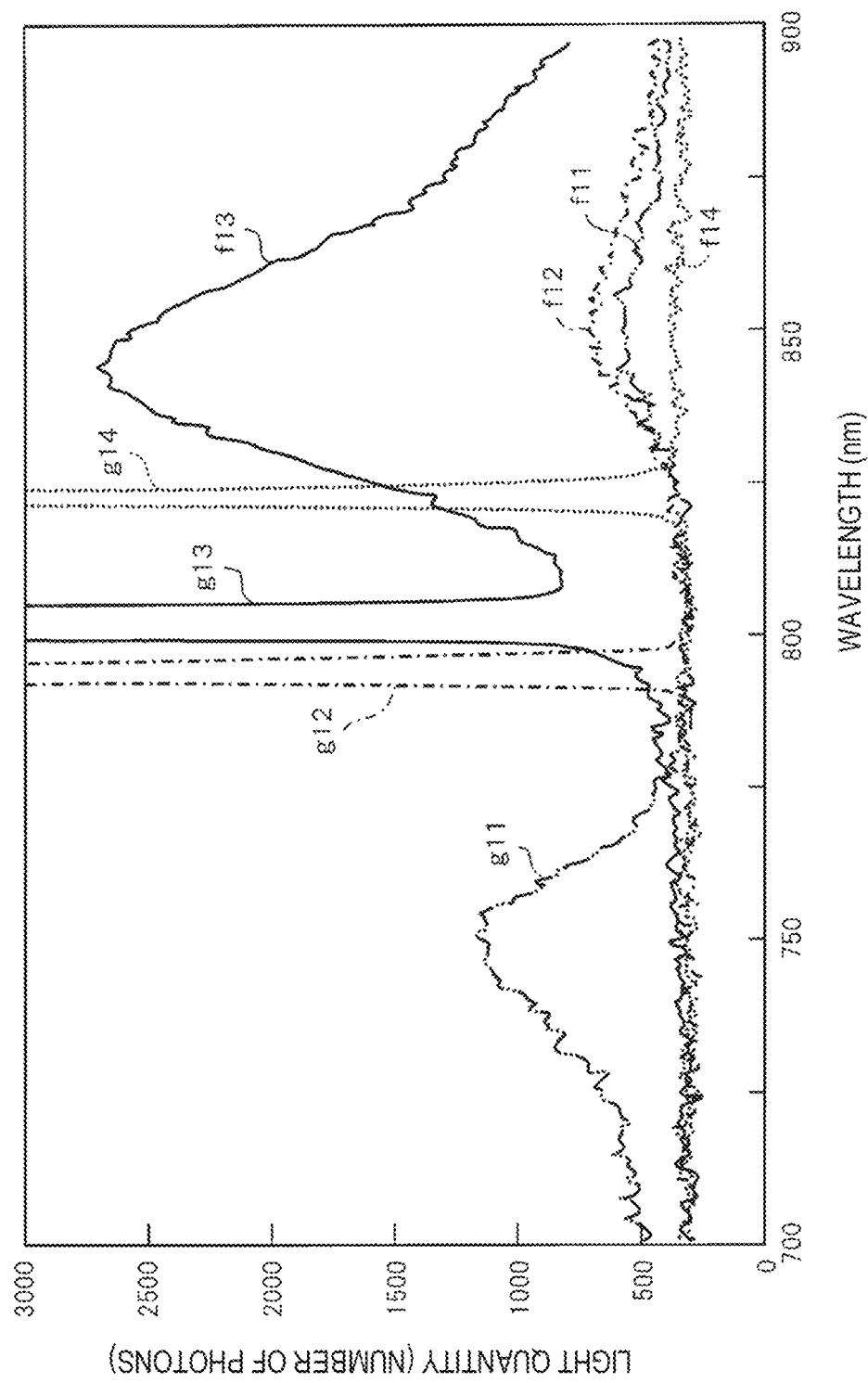
FIG. 8 is a graph showing characteristics of excitation lights and ICG transmitted lights.
Figure 9:
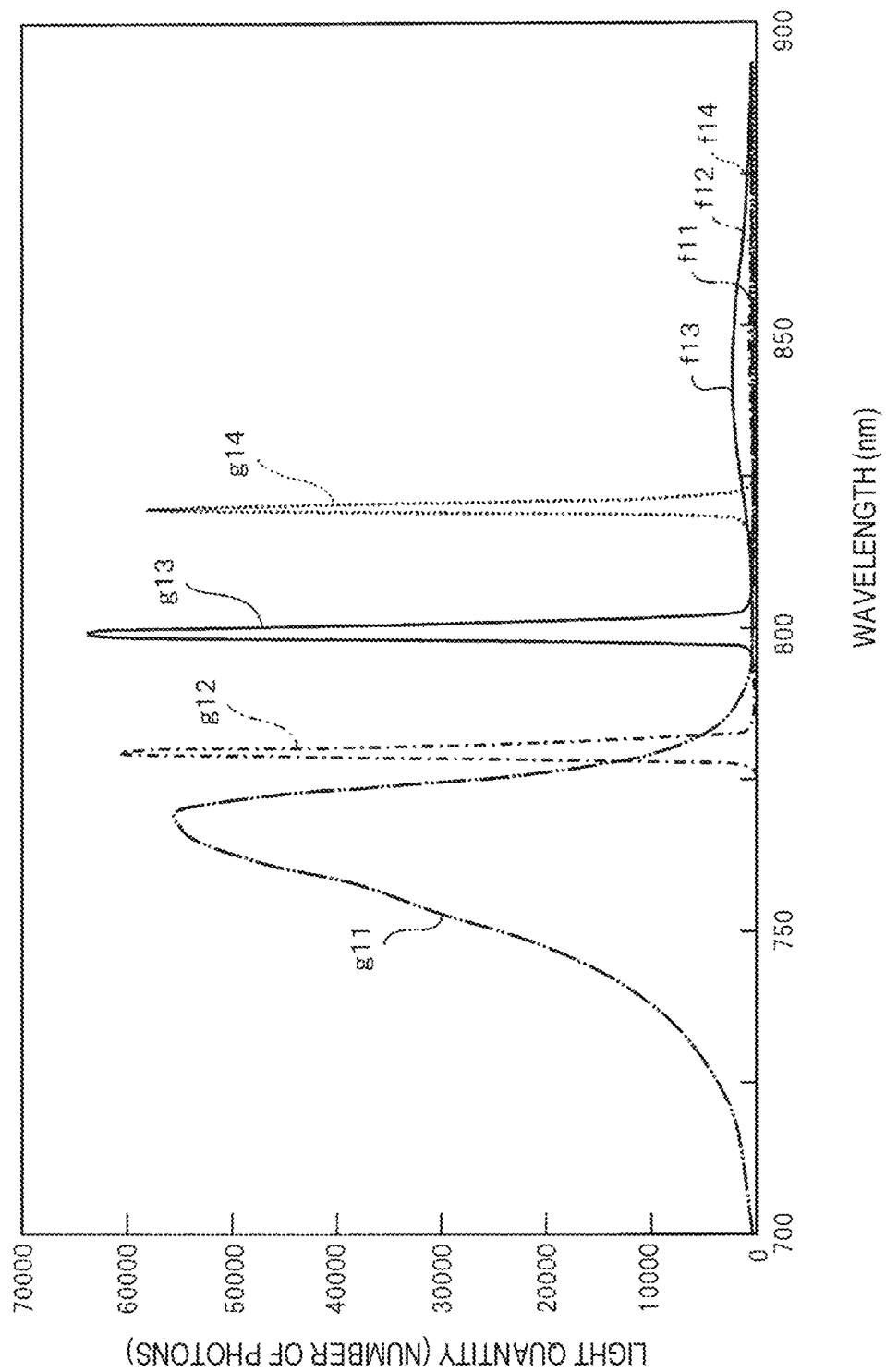
FIG. 9 is a graph showing characteristics of the excitation lights and the ICG transmitted lights in the case where a light quantity of LED light is amplified and a peak value of the amplified LED light is about the same degree as that of each of laser lights.

FIG. 8 is a graph showing an example of characteristics of excitation lights (LED light and laser lights) and ICG transmitted lights. FIG. 9 is a graph showing characteristics of the excitation lights and the ICG transmitted lights in a case where a light quantity of the LED light in the case of FIG. 8 is increased so that a peak value of the LED light can be about the same degree as each of peak values of the laser lights. In each of the graphs, the ordinate expresses light quantity (the number of photons) and the abscissa expresses wavelength (nm).

In FIG. 8 and FIG. 9, a measurement result using LED light having a wavelength of 760 nm and a measurement result using laser light having a wavelength of 823 nm are shown as comparative examples. The LED light mentioned herein does not satisfy the condition of a narrow band according to the embodiment. The laser light with the wavelength of 823 nm does not satisfy the condition of the excitation light wavelength range according to the embodiment.

Figure 11:
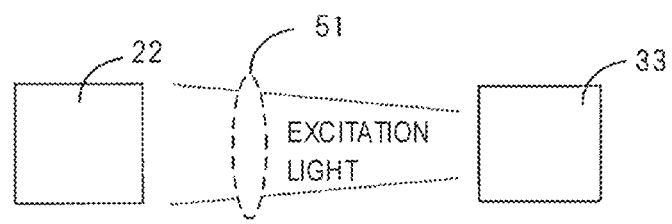
FIG. 11 is a view showing a state in which an image sensor receives IR excitation lights through an ICG solution.

During measurement in order to obtain results shown in FIG. 8 and FIG. 9, the LED light and the laser lights emitted from the IR excitation light source 33 are received by the image sensor 22 through an ICG solution 51 given to the target TG (see FIG. 11). Here, lights (transmitted) through the ICG solution 51 will be also referred to as the ICG transmitted lights. The image sensor 22 receives the ICG transmitted lights through the target TG based on the excitation lights emitted from the IR excitation light source 33. The quantity of each of the received lights by the image sensor 22 corresponds to the number of photons.

In FIG. 8 and FIG. 9, the LED light and the laser lights are used as the excitation lights. The LED light is broadband light whose peak value is relatively small, for example, to be 1,200 counts (CTS) in FIG. 8. On the other hand, each of the laser lights is narrowband light whose peak value is extremely large, for example, to be 60,000 CTS or more.

As shown in FIG. 8, when the LED light with the wavelength of 760 nm is used as excitation light, the target TG is irradiated with broadband LED light g11 having a peak at the wavelength of 760 nm. Due to the irradiation, fluorescence f11 having a peak at the wavelength of 850 nm is emitted from the target TG.

Incidentally, light having the wavelength range of 750 nm to 810 nm (wavelengths pertaining to an approximately right half of a waveform of the LED light) is absorbed by the ICG solution 51 due to contribution to fluorescence emission. As a result, a light detection amount of the wavelength range is reduced. In addition, light intensity of the LED light is lower than that of each of the laser lights. Accordingly, light intensity of fluorescence emission obtained from the LED light is also lower than light intensity of fluorescence emission obtained from the laser light.

In addition, when laser light g12 with the wavelength of 780 nm is used as excitation light, the target TG is irradiated with the narrowband laser light g12 having a peak at the wavelength of 780 nm. Due to the irradiation, a slightly larger amount of fluorescence f12 having a peak at the wavelength of 850 nm is emitted from the target TG than that in the case of the LED light.

In addition, in the case where laser light g13 having the wavelength of 808 nm is used as excitation light, the target TG is irradiated with the narrowband laser light g13 having a peak at the wavelength of 808 nm. Due to the irradiation, a large amount of fluorescence f13 having a peak value at a wavelength of 840 nm is emitted from the target TG in comparison with the case of the LED light.

In addition, in the case where laser light g14 having a wavelength of 823 nm is used as excitation light, the light having the wavelength of 823 nm has little contribution to fluorescence emission. Accordingly, fluorescence f14 emitted from the target TG is substantially absent. That is, the fluorescence f14 is not emitted.

In FIG. 9, characteristics of the ICG transmitted lights generated in reaction to the excitation lights are the same as those in FIG. 8 except that the light quantity of the LED light is increased. In FIG. 9, the light quantity of the fluorescence f11 emitted from the target TG cannot be visually recognized easily due to a difference in scale factor of the ordinate from FIG. 8. However, the light quantity of the fluorescence f11 is also larger in accordance with an increase in the light quantity of the excitation light based on the LED light.

Figure 10:
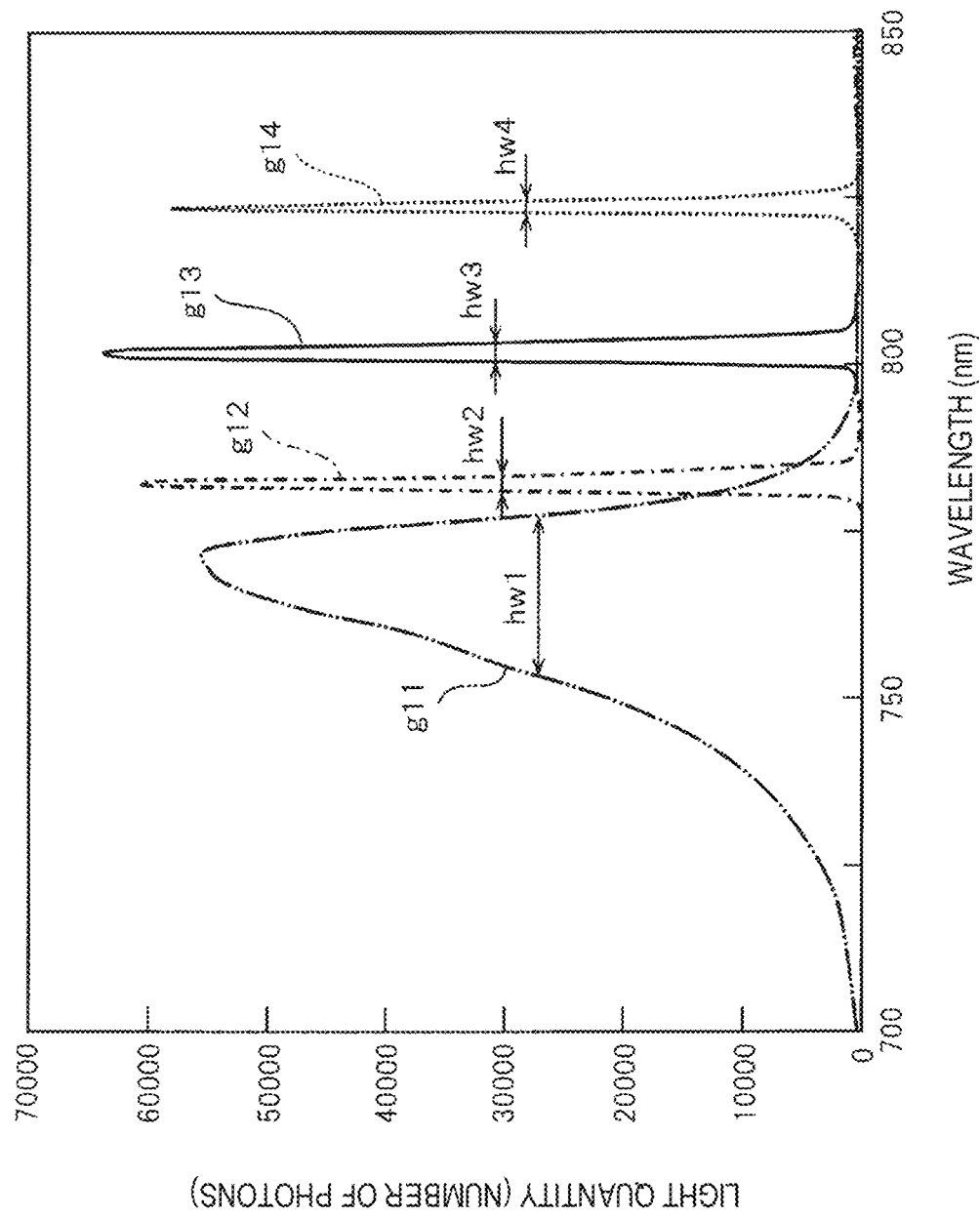
FIG. 10 is a graph showing comparison between a half width of LED light and half widths of laser lights.
Figure 12:
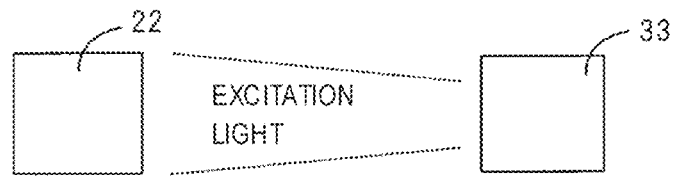
FIG. 12 is a view showing a state in which the image sensor receives IR excitation lights not through the ICG solution.

FIG. 10 is a graph showing comparison between a half width of LED light and half widths of laser lights. During measurement in order to obtain results shown in FIG. 10, the LED light and the laser lights emitted from the IR excitation light source 33 are received by the image sensor 22 not through the ICG solution 51 given to the target TG (see FIG. 12). Incidentally, in FIG. 10, a measurement result using the LED light with the wavelength of 760 nm and a measurement using the laser light with the wavelength of 823 nm are shown as comparison examples in the same manner as in FIG. 8 and FIG. 9.

In each of the signals, for example, a half width is used as an index indicating sharpness of a peak waveform. Broadband light having a peak at a wavelength of 760 nm is illustrated as the LED light by way of example. A half width hw1 of the LED light is 25 nm.

On the other hand, narrowband lights having peaks at wavelengths of 780 nm, 808 nm and 823 nm are illustrated as the laser lights by way of example. A half width hw2 of the laser light with the wavelength of 780 nm is 2.5 nm. A half width hw3 of the laser light with the wavelength of 808 nm is 2.6 nm. A half width hw4 of the laser light with the wavelength of 823 nm, which is a comparison example, is 2.0 nm. Thus, the half width of each of the laser lights is about one tenth as large as the half width of the LED light.

Thus, in the case where each of the laser lights is light included in the wavelength band in which fluorescence emission is generated in the target (TG), a large amount of the fluorescence emission can be obtained from the target. On the other hand, in the case where the laser light is light not included in the wavelength band in which fluorescence emission is generated in the target (TG), there is a possibility that the fluorescence emission can be hardly obtained from the target. For example, the excitation light with the wavelength of 823 nm shown in the comparison example has little contribution to fluorescence emission (see the fluorescence f14 emitted from the target in FIG. 8). On the other hand, the excitation light with the wavelength of 808 nm contributes to a large amount of fluorescence emission including a peak wavelength at the wavelength of 840 nm (see the fluorescence f13 emitted from the target in FIG. 8).

Incidentally, the wavelength band of each of the excitation lights is shifted due to a body composition, a region, and a health condition etc. of the target TG. Accordingly, sufficient fluorescence emission may not be always obtained based on the laser light with the wavelength of 808 nm used as excitation light. Therefore, when laser lights having at least two different wavelengths (e.g. 780 nm and 808 nm) are used as excitation lights, the possibility that one of the excitation lights may contribute to fluorescence emission becomes higher, and the possibility that the light quantity of the fluorescence emitted from the target may increase becomes higher. When the number of the excitation lights is increased, the possibility that the light quantity of the fluorescence emitted from the target may increase becomes higher.

[Effects etc.]

In the endoscope system 5 configured thus according to the embodiment, the IR excitation light source 33 (non-visible light source) emits, onto the target (subject to be inspected), the laser light (an example of first excitation light having a first wavelength of a non-visible light band) which has a wavelength of 780 nm and whose half width is not more than 10 nm, and the laser light (an example of second excitation light having a second wavelength of the non-visible light band different from the first wavelength) which has a wavelength of 808 nm and whose half width is not more than 10 nm. The image sensor 22 is excited by at least one of the laser light having the wavelength of 780 nm and the laser light having the wavelength of 808 nm to thereby generate an image including the target from which the fluorescence is emitted. The monitor 40 (an example of an output device) outputs the generated image.

Thus, when each of the wavelength bands of the excitation lights is set as a narrow band so that a half width of the excitation light can be not more than 10 nm, a component of the excitation light can be prevented from being present in the wavelength band of the fluorescence emission. Accordingly, the endoscope system 5 can suppress imaging of the fluorescence emission from being hindered by the excitation lights. Consequently, the endoscope system 5 can perform fluorescence imaging on the target using the different narrowband excitation lights, and can improve accuracy of the fluorescence imaging. In addition, in the endoscope system 5, the excitation lights having the plurality of wavelengths are used. Therefore, the wavelength band suitable for fluorescence emission is not removed so that fluorescence emission can be generated easily.

In addition, the IR excitation light source 33 may have the LD 25A which emits the laser light with the wavelength of 780 nm, and the LD 25B which emits the laser light with the wavelength of 808 nm.

When the endoscope system 5 is thus provided with a plurality of light sources, the light intensity of the laser light with the wavelength of 780 nm and the light intensity of the laser light with the wavelength of 808 nm can be increased. Consequently, the endoscope system 5 can increase the light intensity of the fluorescence emission to thereby facilitate fluorescence imaging. In addition, the endoscope system 5 can adjust the light quantity of the laser light with the wavelength of 780 nm and the light quantity of the laser light with the wavelength of 808 nm independently of each other. Thus, the light quantities of the laser lights with the wavelengths 780 nm and 808 nm can be set at light quantity values suitable for fluorescence emission so that efficiency of the fluorescence emission can be enhanced.

In addition, the non-visible light source may be a laser diode.

Thus, the endoscope system 5 can increase the light intensities of the excitation lights to thereby increase the light intensity of the fluorescence emission. Accordingly, fluorescence imaging of the subject to be inspected can be performed easily. In addition, since each of the light intensities of the excitation lights is increased, the size of the image sensor 22 can be reduced and the size of the distal end of the endoscope 10 can be reduced in the endoscope system 5. Accordingly, the endoscope system 5 can reduce invasion into the patient which is the subject to be inspected.

In addition, the endoscope system 5 may be provided with the IR excitation light cut filter 23 (an example of an optical filter) which is disposed on the incidence side of the image sensor 22 to shield the laser light with the wavelength of 780 nm and the laser light with the wavelength of 808 nm. The IR excitation light cut filter 23 may have a characteristic that transmittance of the IR excitation light cut filter 23 is not higher than 0.1% with respect to light in the wavelength range of 690 nm to 810 nm.

Thus, the endoscope system 5 can shield the laser light with the wavelength of 780 nm and the laser light with the wavelength of 808 nm without shielding the fluorescence emission having a wavelength longer than 810 nm. Accordingly, the user can more clearly image the fluorescence emission of the subject to be inspected.

Thus, in the endoscope system 5, the ICG may be used to cause fluorescence emission in the target TG. In this manner, the endoscope system 5 can use any general-purpose item used for fluorescence emission. Thus, the endoscope system 5 can perform fluorescence imaging inexpensively.

In addition, each of the laser light with the wavelength of 780 nm and the laser light with the wavelength of 808 nm may have any wavelength within the excitation light wavelength band of 750 nm to 810 nm suitable for the fluorescence emission. In addition, a difference between the laser lights may be 20 nm or more (an example of a predetermined value or more).

Thus, a difference between the wavelength of the first excitation light and the wavelength of the second excitation light is 20 nm or more. Accordingly, the endoscope system 5 can widely cover the excitation light wavelength band (750 nm to 810 nm) suitable for the fluorescence emission. Accordingly, the endoscope system 5 can prevent shortage of a light quantity of the fluorescence emission from occurring due to the two laser lights inclined to the wavelength band which has little contribution to the fluorescence emission.

In addition, the image sensor 22 may be disposed at the distal end portion (the distal end portion of the scope 13) of the endoscope 10.

Thus, in comparison with a method of using a relay lens or an optical fiber to guide light to a camera at user's hand in a background-art endoscope system, the endoscope system 5 can suppress reduction of the light intensity of the fluorescence emission incident on the image sensor 22, to thereby increase the light reception quantity of the fluorescence. Accordingly, the size of the image sensor 22 for obtaining the same light reception quantity can be also reduced. In this case, the endoscope system 5 can improve the accuracy of the fluorescence imaging more greatly.

In addition, when the relay lens is used, the fluorescence imaging device cannot have flexibility. As a solution to such a problem, the flexible portion 11 can be provided on a rear side of the portion where the sensor is disposed. Thus, a camera unit built in the endoscope system 5 can be also brought nearby a region to be observed or in a desired direction.

In addition, the size of the image sensor 22, i.e. the radial-direction length of the image sensor 22 disposed inside the scope 13 may be 10 mm or less.

Thus, the image sensor 22 can be applied to the endoscope 10 in the endoscope system 5. In addition, even when the size of the image sensor 22 is 10 mm or less, the endoscope system 5 can image the fluorescence emission excited by high intensity light such as laser light so as to secure the accuracy of the fluorescence imaging.

In addition, the endoscope system 5 may be provided with the visible light source 34 (an example of a visible light source) emitting visible light onto the target. The image sensor 22 may generate a first image containing the target by first photoelectric conversion using visible light, and generate a second image containing the target by second photoelectric conversion using non-visible light.

Thus, even if the subject to be inspected is a dark place inside the body, the endoscope system 5 can cooperate with a fluorescence emission portion to use the visible light to image the entire subject to be inspected.

Incidentally, in addition to a device (endoscope, endoscope system) category, the embodiment can be also applied to another category (e.g. a method (a fluorescence imaging method)).

Although the embodiment has been described above with reference to the drawings, it is a matter of course that the invention is not limited to such an example. It is obvious that those skilled in the art can arrive at various change examples or modification examples without departing from the scope described in Claims. Accordingly, it should be understood that the various change examples or modification examples surely belong to the technical scope of the invention.

Although the case where the endoscope 10 is provided with the IR excitation light cut filter 23 has been described by way of example in the first embodiment, the IR excitation light cut filter 23 may be removed.

Although the case where separate light sources, i.e. the LD 25A and the LD 25B, are provided as the light sources emitting the IR excitation lights has been described by way of example in the first embodiment, an integrated light source may be used alternatively. That is, one light source may emit different IR excitation lights.

In the first embodiment, the laser lights having two wavelengths (780 nm and 808 nm) have been described by way of example. However, allocation of the light intensities (light quantities) of the laser lights can be set desirably. The light quantities of the laser lights can be allocated, for example, by the controller 31. Accordingly, the endoscope system 5 can irradiate the target with the excitation lights with the light quantities suitable for the fluorescence whose peak position changes according to the body composition, the region, the health condition, etc. of the target.

In the first embodiment, the case where the narrowband excitation lights are obtained due to the laser lights emitted from the LDs respectively has been described by way of example. Incidentally, the endoscope system 5 may use a spectral filter to extract specific wavelength light from the broadband light (LED light) emitted from the LED to thereby obtain narrowband (e.g. with a half width of not more than 10 nm) excitation lights. The LED light may be amplified by an amplifier etc. In addition, the endoscope system 5 may combine laser light emitted from at least one LD and the specific wavelength light extracted from the LED light by the spectral filter to thereby obtain a plurality of narrowband excitation lights. Thus, the endoscope system 5 can use even a small number of LDs to easily obtain narrowband excitation lights having various wavelengths.

In the first embodiment, the case where the ICG is given as an optical contrast agent in vivo has been described by way of example. However, another optical contrast agent than the ICG may be given. In this case, a spectral characteristic in a wavelength region of non-visible light may be determined in accordance with wavelengths of excitation lights for exciting the optical contrast agent. In this case, the IR excitation light cut filter 23 may have another characteristic than the characteristic shown in FIG. 5.

In the first embodiment, the case where the endoscope 10 is a soft endoscope having the soft portion 11 has been described by way of example. However, the endoscope 10 may be an endoscope having another characteristic. For example, the endoscope 10 may be a hard endoscope from which the soft portion 11 is absent.

In the first embodiment, the chemical emitting fluorescence in the wavelength region of the infrared light is used. However, another chemical emitting fluorescence in a wavelength region of ultraviolet light may be used alternatively. Even when the ultraviolet light is used, the endoscope 10 can take an image of an affected part from which fluorescence is emitted, in the same manner as in the case where the optical contrast agent emitting fluorescence in a wavelength region of near infrared light is used.

In the first embodiment, the monitor which can display a fluorescence emission image and a visible light image on the screen is shown as an output device. However, the output device is not limited to the monitor. The output device may be a printer which can print the fluorescence emission image and the visible light image, a signal output device which can output respective image signals of the fluorescence emission image and the visible light image, a storage device which can store respective image data of the fluorescence emission image and the visible light image in a recording medium, etc.

In the first embodiment, the monitor 40 may be capable of displaying the respective graphs shown in FIG. 8, FIG. 9 and FIG. 10. In this case, the light quantity (the number of photons) in the ordinate may be displayed normally. However, it may be logarithmically expressed alternatively. When it is logarithmically expressed, LED light having a small light quantity at a peak and laser light having a large light quantity at a peak can be displayed dynamically on one and the same graph. In addition, the light quantities of the respective graphs may be expressed by relative values (e.g. of peak values of a plurality of laser lights, a largest one may be defined as a relative value 100).

In the first embodiment, a processor such as the controller 31, the image processor 35 or the display processor 36 may have any physical configuration. In addition, when a programmable processor is used, processing contents can be changed by change of programs from one to another. Accordingly, the degree of freedom for design of the processor can be enhanced. The processor may be constituted by one semiconductor chip or may be physically constituted by a plurality of semiconductor chips. When the processor is constituted by the plurality of semiconductor chips, the respective controls in the first embodiment may be achieved by the semiconductor chips separately and respectively. In this case, it is conceivable that one processor is constituted by the plurality of semiconductor chips. In addition, the processor may be constituted by the semiconductor chips and a member (such as a capacitor) having another function. In addition, one semiconductor chip may be configured to realize functions provided by the processor and other functions than the processor functions. The processors may be constituted by one processor.

Figure 13:
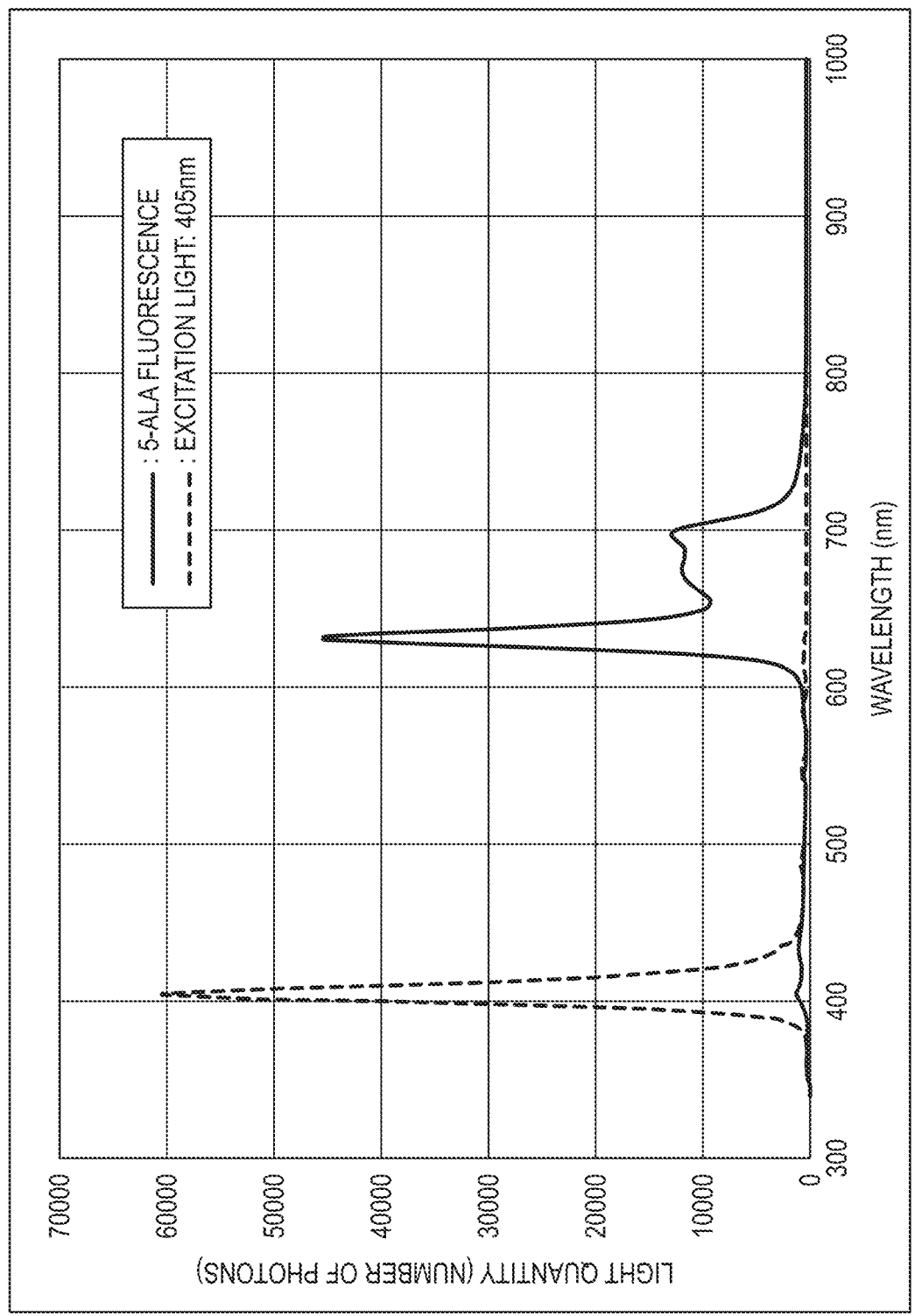
FIG. 13 is a graph showing a characteristic of 5-ALA fluorescence.
Figure 14:
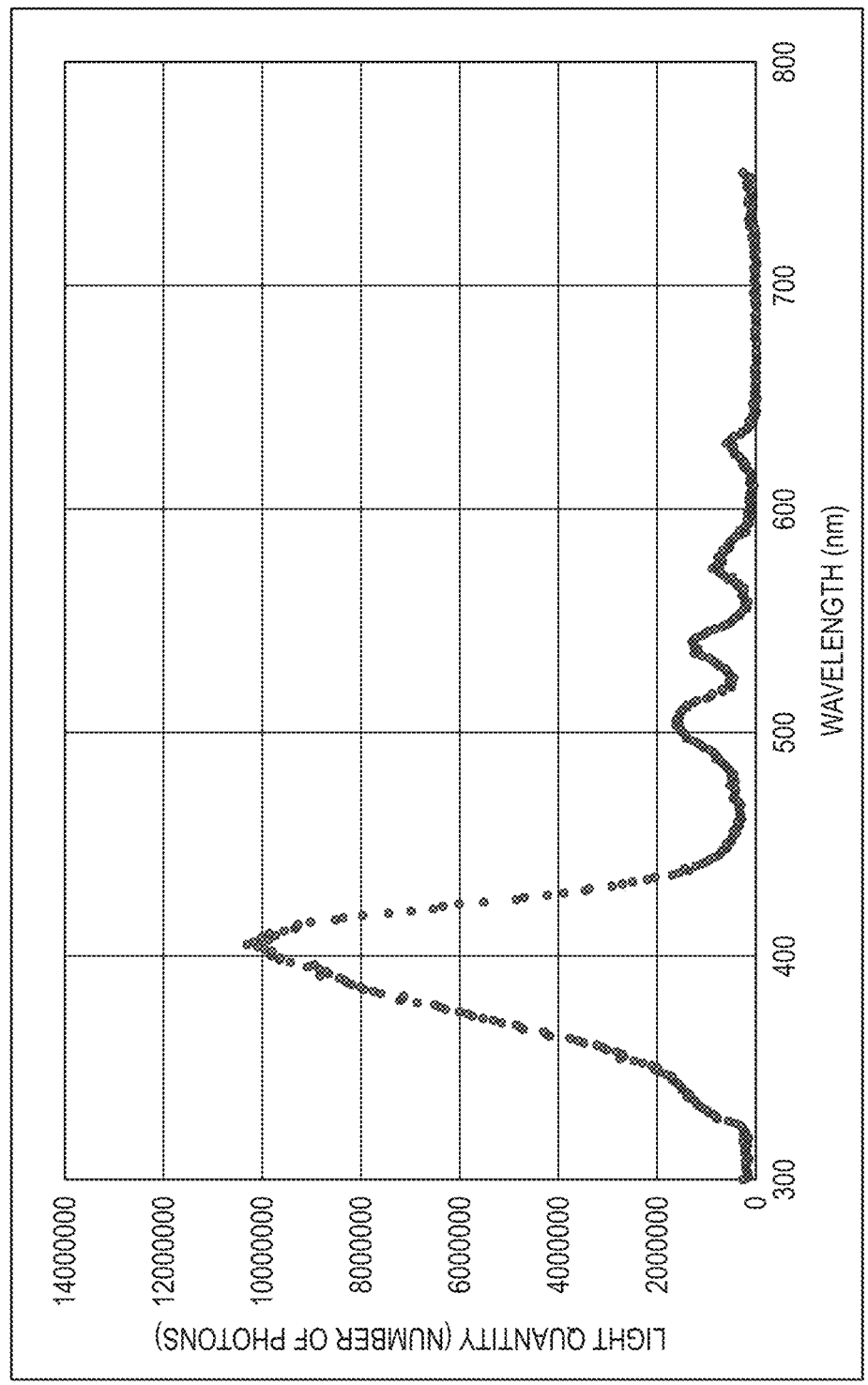
FIG. 14 is a graph showing a characteristic of 5-ALA excitation light.

When intraoperative fluorescence diagnosis of a tumor is performed using 5-aminolevulinic acid (5-ALA) during tumor excision of malignant glioma, the 5-ALA is orally given to a patient prior to craniotomy for the tumor excision. Then, the 5-ALA absorbed in vivo is taken into the malignant glioma and converted into protoporphyrin IX (PpIX) by Heme metabolic enzyme in tumor cells. As long as light with a wavelength of 405 nm is included in light emitted from the visible light source 34 toward an operative field as shown in FIG. 13, fluorescence occurs from the PpIX accumulated in the tumor cells so that the tumor cells can be identified. Thus, a PpIX-specific wavelength peak (630 nm) can be detected without affecting ICG fluorescence so that imaging can be performed using two fluorescent lights of the ICG and the 5-ALA. On this occasion, efficiency of excitation light has an intensive peak at 405 nm, as shown in FIG. 14. Accordingly, the intensity of the occurring fluorescence is enhanced. Therefore, when semiconductor laser light or narrowband LED light having a peak wavelength of 405 nm is radiated, fluorescence can be generated efficiently. However, 405 nm is a wavelength of the visible light to affect an RGB white image to be observed. Accordingly, by use of an ultraviolet ray absorbing filter (SC filter SC42 made by FUJIFILM Corporation), the influence of the excitation light can be also reduced.

The present disclosure is useful for an endoscope system and a fluorescence imaging method etc. in which reduction of light intensity of fluorescence emission generated by a target can be inhibited so that accuracy of fluorescence imaging can be improved.

What is claimed is:

1. An endoscope system, comprising:
a non-visible light source configured to emit first excitation light and second excitation light onto a target in which a fluorescent chemical having a wavelength band being capable of emitting fluorescence has been given, the first excitation light having a half width of not more than 10 nm and a first wavelength of a non-visible light band, the second excitation light having a half width of not more than 10 nm and a second wavelength of the non-visible light band being different from the first wavelength, a difference between the first wavelength and the second wavelength being at least 20 nm, each of the first wavelength and the second wavelength being within a first range of 750 nm to 810 nm;
an image sensor configured to generate an image including the target excited by at least one of the first excitation light and the second excitation light such that fluorescence of the fluorescent chemical is emitted;
an optical filter that is disposed on an incidence side of the image sensor and that is configured to shield the first excitation light and the second excitation light, wherein the optical filter has a characteristic that transmittance of the optical filter is not higher than 0.1% with respect to the wavelengths of light throughout a second range of 690 nm to 810 nm, the optical filter providing for transmittance of light at least throughout a third range from 380 nm to 690 nm and a fourth range including 830 nm; and
an output configured to output the image.

2. The endoscope system according to claim 1, wherein: the non-visible light source has a first light source configured to emit the first excitation light and a second light source configured to emit the second excitation light.

3. The endoscope system according to claim 1, wherein: the non-visible light source is a laser diode.

4. The endoscope system according to claim 1, wherein: ICG (IndoCyamine Green) is used to cause fluorescence emission in the target.

5. The endoscope system according to claim 1, wherein: the image sensor is disposed at a distal end portion of an endoscope.

6. The endoscope system according to claim 5, wherein: a length of a diagonal of the image sensor having a square shape is equal to or smaller than 10 mm.

7. The endoscope system according to claim 1, further comprising:
a visible light source configured to emit visible light onto the target, wherein:
the image sensor is configured to generate a first image including the target by first photoelectric conversion using the visible light, and is configured to generate a second image including the target by second photoelectric conversion using non-visible light that is derived from fluorescence emission of the target excited by at least one of the first excitation light and the second excitation light.

8. A fluorescence imaging method in an endoscope system, the fluorescence imaging method comprising:
emitting first excitation light and second excitation light onto a target in which a fluorescent chemical having a wavelength band being capable of emitting fluorescence has been given, the first excitation light having a half width of not more than 10 nm and a first wavelength of a non-visible light band, the second excitation light having a half width of not more than 10 nm and a second wavelength of the non-visible light band being different from the first wavelength, a difference between the first wavelength and the second wavelength being at least 20 nm, each of the first wavelength and the second wavelength being within a first range of 750 nm to 810 nm;
shielding the first excitation light and the second excitation light via an optical filter having a characteristic that transmittance of the optical filter is not higher than 0.1% with respect to the wavelengths of light throughout a second range of 690 nm to 810 nm, the optical filter providing for transmittance of light at least throughout a third range from 380 nm to 690 nm and a fourth range including 830 nm;
generating an image including the target that is excited by at least one of the first excitation light and the second excitation light such that fluorescence of the fluorescent chemical is emitted; and
outputting the image.

* * * * *